(12) United States Patent
Lepple-Wienhues

(10) Patent No.: US 10,589,030 B2
(45) Date of Patent: Mar. 17, 2020

(54) DEVICE FOR ATTACHMENT TO A PORTABLE LIQUID INJECTION DEVICE

(71) Applicant: Valtronic Technologies (Holding) SA, Les Charbonnières (CH)

(72) Inventor: Albrecht Lepple-Wienhues, Pontarlier (FR)

(73) Assignee: Valtronic Technologies (Holding) SA, Les Charbonnieres (CH)

( * ) Notice: Subject to any disclaimer, the term of this patent is extended or adjusted under 35 U.S.C. 154(b) by 0 days.

(21) Appl. No.: 15/502,076

(22) PCT Filed: Jul. 31, 2015

(86) PCT No.: PCT/EP2015/067637
§ 371 (c)(1),
(2) Date: Feb. 6, 2017

(87) PCT Pub. No.: WO2016/020276
PCT Pub. Date: Feb. 11, 2016

(65) Prior Publication Data
US 2017/0224922 A1    Aug. 10, 2017

(30) Foreign Application Priority Data

Aug. 7, 2014  (EP) ..................................... 14180261
May 4, 2015  (EP) ..................................... 15166201

(51) Int. Cl.
*A61M 5/31*    (2006.01)
*G01F 23/26*   (2006.01)
(Continued)

(52) U.S. Cl.
CPC ................ *A61M 5/31* (2013.01); *A61M 5/24* (2013.01); *A61M 5/31568* (2013.01);
(Continued)

(58) Field of Classification Search
CPC ................ A61M 5/31; A61M 5/31568; A61M 2205/52; A61M 2205/3372;
(Continued)

(56) References Cited

U.S. PATENT DOCUMENTS 4,237,878 A  *  12/1980  Kobayashi .......... A61M 5/1684
128/DIG. 13
6,110,148 A      8/2000  Brown et al.
(Continued)

FOREIGN PATENT DOCUMENTS

| DE | 10 2004 040 441 A1 | 6/2006 |
|----|---|---|
| EP | 1762258 A1 | 3/2007 |
| JP | 2009529999 A | 8/2009 |
| WO | 2013/138830 A1 | 9/2013 |
| WO | 2014/052997 A1 | 4/2014 |

OTHER PUBLICATIONS

International Search Report and Written Opinion issued for International patent application No. PCT/EP2015/067637, dated Dec. 3, 2015, 12 pages.

*Primary Examiner* — Lauren P Farrar
(74) *Attorney, Agent, or Firm* — Duane Morris LLP

(57) ABSTRACT

The invention refers to a device for attachment to a portable liquid injection device, wherein said device is designed to enclose the drug reservoir of the injection device completely. Further, said device has at least two flat conductive electrodes enabling an electrical field to be applied across the entire volume of the drug reservoir of the injection device. In particular, the portable liquid injection device is a so-called insulin pen, i.e. a portable liquid injection device which is used to inject insulin for the treatment of diabetes. The inventive device preferably is in the form of a cap, in particular in the form of a cap of an insulin pen.

19 Claims, 6 Drawing Sheets

Figure 1:
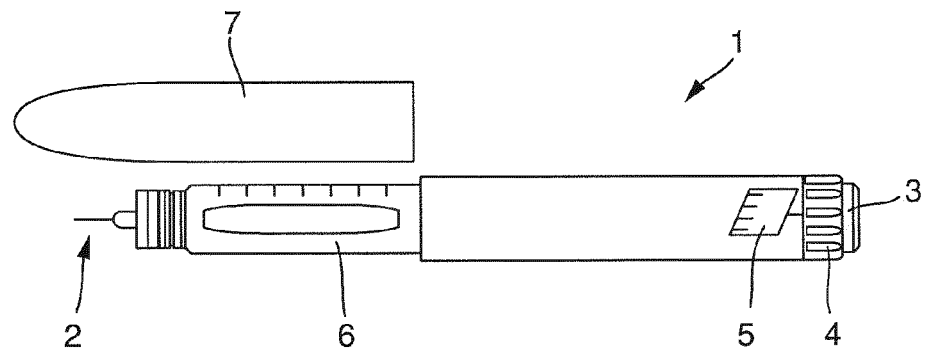

(51) Int. Cl.
*A61M 5/32* (2006.01)
*A61M 5/24* (2006.01)
*A61M 5/315* (2006.01)
*A61M 5/168* (2006.01)
*A61M 5/145* (2006.01)

(52) U.S. Cl.
CPC ......... *A61M 5/3202* (2013.01); *G01F 23/266* (2013.01); *G01F 23/268* (2013.01); *A61M 5/1452* (2013.01); *A61M 5/1684* (2013.01); *A61M 2205/3317* (2013.01); *A61M 2205/3372* (2013.01); *A61M 2205/3389* (2013.01); *A61M 2205/52* (2013.01)

(58) Field of Classification Search
CPC ... A61M 2205/3389; A61M 2205/3317; G01F 23/268; G01F 23/266
See application file for complete search history.

(56) References Cited

U.S. PATENT DOCUMENTS

| | | | |
|---|---|---|---|
| 9,395,716 B2 * | 7/2016 | Bammer | A61M 5/1684 |
| 2002/0096543 A1 * | 7/2002 | Juselius | A61J 7/0481 |
| | | | 222/631 |
| 2007/0123829 A1 * | 5/2007 | Atterbury | A61M 5/31535 |
| | | | 604/207 |
| 2011/0276281 A1 * | 11/2011 | Wernet | G01F 23/241 |
| | | | 702/55 |
| 2013/0310756 A1 | 11/2013 | Whalley et al. | |
| 2014/0018733 A1 | 1/2014 | Sjolund | |
| 2015/0045727 A1 * | 2/2015 | Bammer | A61M 5/31525 |
| | | | 604/67 |

\* cited by examiner

State of the art

State of the art $C_{total} = C2$ $C_{total} = 1/(2/(C1)+1/(2\,C3+C2))$

DEVICE FOR ATTACHMENT TO A PORTABLE LIQUID INJECTION DEVICE

CROSS-REFERENCE TO RELATED APPLICATIONS

The present application is a U.S. national phase application filed under 35 U.S.C. § 371 of International Application No. PCT/EP2015/067637, which was filed Jul. 31, 2015 and which claims priority to European Patent (EP) Application No. 15166201.2 filed on May 4, 2015 and EP Application No. 14180261.1 filed on Aug. 7, 2014, each of which are incorporated herein by reference in their entirety.

FIELD OF THE INVENTION

This invention relates to a device for attachment to a portable liquid injection device. In particular, the inventive device is for attachment to a so-called insulin pen.

Further, the invention relates to a portable liquid injection device, in particular an insulin pen, comprising the inventive device.

BACKGROUND TO THE INVENTION

Many drugs must be administered parenterally, because they are either not resorbed sufficiently or destroyed in the gastrointestinal tract. Typical examples include peptide drugs like insulin. Therefore, in the following the invention is described in the context of an insulin pen, although it extends to other drug delivery devices and drugs.

The pharmacological half-life of these drugs often is very short, leaving the need for multiple daily injections. Therefore, often the injections are performed by the patient himself instead of trained medical professionals. An insulin-dependent diabetic patient e.g. needs to inject multiple times a day at variable doses, adjusted to food intake and physical activity.

To comfort these frequent variable dose self-administrations drug delivery devices have been introduced that are easy to use and typically comprise a reservoir with a plunger, a hypodermic needle and a dosing mechanism. A typical example for such devices is called an "insulin pen". These pens are critical medical devices for the reason that both an overdose and underdose can lead to severe health problems including death. Therefore, those devices are mostly kept very reliable and independent of e.g. battery charge. Most insulin pens on the market today have a strictly mechanic dosing mechanism.

While these injection pens facilitate the multiple injections required, it is difficult and cumbersome for the patient to keep records of all parameters determining the insulin dose adjustment required. Even keeping track of the injection time and dose itself becomes a demanding task, since the typical drug delivery devices do not include means for data communication nor memory. Therefore, it is not rare that a patient does not remember dose, time or the sheer fact of injection in daily life. Severe effects of overdosing or omitted administrations are therefore not rare events and threaten health and life of these patients.

Further, a patient may use one, two or even three different pens during the day. A typical example for a dosage pattern is as follows: In the morning the patient injects a dose of long-lasting insulin with his/her first pen. During the day he/she further injects multiple doses of rapid acting insulin before each meal using a different pen. Timing and doses are typically similar from day to day for the same patient. Deviation from this pattern would be dangerous. The wrong pen/insulin type could be used or the wrong dose injected, or the injection either forgotten or doubled.

In the prior art, DE-A1-10 2004 040 441 discloses a method for determining the filling level of a substance in an ampoule comprising at least two electrodes, whereby the filling level is determined by measuring the capacity of at least one condenser which is formed by said at least two electrodes. According to this publication, the electrodes are located directly in an injection device containing the ampoule, or, preferably, the electrodes are located on the ampoule, in particular are integrated into the ampoule.

As a consequence, the disclosure of DE-A1-10 2004 040 441 requires an integration of electronics into the injection device, making the device more complex and failure prone. For example, the function of the injection device will depend on the availability of a charging current, or a charged power source, and, therefore, will be less reliable than a classical injection device (e.g. insulin pen) with a mechanical dosing mechanism.

WO-A1-2013138830 describes a capacitive NFC (Near Field Communication)-based fill-level sensor for insulin pens. This publication is based on the same technical principle for determining the filling level of the insulin in an ampoule as shown in DE-A1-10 004 040 441. For this purpose, at least two electrodes are located on the ampoule or directly inside of the part of the pen holding the ampoule.

The invention disclosed in WO-A1-2013138830 is inter alia defined by the presence of two antennas allowing the transmittance of measured values to an external data communications unit via NFC.

US-A1-20140018733 discloses a replaceable cap for a transdermal liquid dosing device such as an insulin pen. The cap body also includes a cavity opening into the interior of the cap body and housing a control unit which includes a timer unit, a switch mechanism and a timer display unit. This specific design of the interior of the cap body (control unit including timer unit, switch mechanism and timer display unit) is supposed to help the user determining whether a given dose has been administered. US-A-20140018733 is silent with respect to the applied quantity of the corresponding substance and to the (remaining) filling level of the substance in the dosing device.

US-A1-20020096543 discloses a portable control device to be mounted externally on a conventional injection pen cap containing a touchless proximity sensor that is located on one side of the cap to detect presence/removal either of the metal needle, the insulin ampoule or an electronic tag implemented in the pen. The control device also includes a transmitter that communicates with a console to control a system of colored lights as feedback and reminder for the patient. The disclosed embodiments are complex to use and learn and may require discarding or adapting the existing insulin delivery systems already in use by the patient. This disclosure is not suitable to achieve precise, sensitive and reproducible readout of the insulin ampoule content required for tracking of the applied dose, because it does not apply an electric field through the entirety of the insulin container homogenously and also does not comprise means to adjust for inhomogeneity or disturbances of said electric field.

OBJECT OF THE INVENTION

The present invention has the object to overcome the described limitations of the discussed prior art. The invention should create the possibility for any user of an injection device, in particular of an insulin pen, to easily determine the filling state of the drug reservoir of the injection device without a complicated construction of this device and without changing the use of existing devices. In particular, it should be possible to determine the filling level of the drug reservoirs of injection devices from different providers with different constructions.

SUMMARY OF THE INVENTION

The present invention provides a device for attachment (attachment device) to a portable liquid injection device, wherein said device is designed to enclose the drug reservoir of the injection device completely. Further, said device has at least two flat conductive electrodes enabling an electrical field to be applied across a part, in particular the entire volume, of the drug reservoir of the injection device.

The term "flat" means that the electrodes, irrespective of their actual shape or design, have a low height or thickness compared to their other two dimensions. Preferably, said flat electrodes have the shape of cylindrical surface segments with a low height or thickness of the actual electrode body.

In particular, the portable liquid injection device is a so-called insulin pen, i.e. a portable liquid injection device which is used to inject insulin for the treatment of diabetes.

The electrical field will be applied across the entire volume of the drug reservoir of the injection device as evenly and homogenously as practical. It is of special importance that the entire volume of the drug reservoir is covered by said electrical field, because any parts of the volume either not penetrated by the field or penetrated only by weak portions of the field will not be measured precisely. Said electrical field will preferably be used for determining the filling level of a substance in the drug reservoir, in particular of a hormone, e.g. insulin (or a solution containing said substance, respectively).

The capacitance changes which can be measured are quite small, e.g. preferably in the subpicoFarad to sub-Femto-Farad range. Further, the signal to noise ratio will be quite small due to unavoidable thermal noise in the capacitor as well as in the measurement electronics. Therefore, this disclosure describes means to reliably, repeatedly and precisely measure those tiny electrical parameters avoiding errors that could affect the determination of the filling level in the drug reservoir down to a statistical error of preferably less than 10 µl, 5 µl, 1 µl, or even 0.5 µl.

In contrast to the methods provided by the prior art, a (separate) device for attachment to a portable liquid injection device is used for determining the filling level of the drug reservoir. In one embodiment this separate device can have the form of a protective cap, replacing the standard protective cap that comes with the device. Therefore, construction and use of the injection device itself need not to be changed for determining the filling level of the drug reservoir. No separate device needs to be added to the pen or its protective cap avoiding the requirement to deal with an additional device. Rather the device will replace the protective cap that already belongs to and comes with the pen. Separate instructions or a separate training for understanding or using the injection device are not necessary. Only the inventive device is used for providing the user of the injection device (patient or health professional) with a complete logged history of dose and time of past injections without any user input required.

It is known that the dielectric constant of water at room temperature is approximately 80 times higher than that of air, and at least an order of magnitude higher than that of glass or plastic. Therefore, the impedance follows closely the volume of water in the drug container. The needle can remain on the pen reservoir for the impedance measurement.

In particular, the electrodes (for stimulating the electrical field) are elongated electrodes, wherein preferably the longest dimension of these (area) electrodes is provided to be parallel with an axis of the injection device, in particular parallel with the longitudinal axis of an insulin pen.

As defined above, at least two (stimulating) electrodes are necessary according to the invention. As a consequence, it is possible to use at least 3, e.g. 3, 5 or 7 electrodes according to the invention. Preferably, the corresponding number of electrodes is distributed along the circumference of the inventive device in regular distances, e.g. 3 electrodes are located on a cylindrical circumferential surface offset by 120°.

With preferred embodiments of the inventive device, the electrodes are provided in pairs, in particular along the circumference of the device, for forming a capacitor. This results in a total number of 2 n electrodes with n≥1, wherein n preferably is between 1 and 10.

As a consequence, said pairs of electrodes form a capacitor where the drug reservoir is a part of the dielectric layer, and, therefore, an AC (Alternating Current) electrical field traversing the drug reservoir can be applied and the impedance of said capacitor can be determined.

The (stimulating) electrodes and/or the electrode pairs can be geometrically arranged and/or electrically switched in a way that allows the electrical field to be applied across the drug reservoir (drug container) in multiple rotational directions perpendicular to an axis of the injection device, in particular, the longitudinal axis of an injection device in the form of a pen, in order to cancel out asymmetrical location of the drug container in any non-homogeneous electrical fields.

This aspect of the present invention will be explained in more detail later.

In particular, it is preferred according to the invention that the inventive device is designed in a way that electrodes, preferably electrode pairs, can be separately switched in a way that the electrical AC field is crossing the drug reservoir perpendicular to an axis of the injection device, preferably to the longitudinal (generally rotational) axis of a pen-like device at different angles, at least at two angles which are 90° apart. This aspect will also be discussed later in more detail.

As a consequence, in the present invention it is not required that the (stimulating) electrodes are mechanically very accurately positioned and oriented with respect to the drug reservoir. In other words: With the inventive device, rotational, axial and lateral tolerances are acceptable when the inventive device is attached to the portable liquid injection device. Surprisingly, it is not required in the present invention that the electrodes are located close to the drug container, or that the electrodes are at a fixed distance to the drug container, or that the electrical field for impedance measurement is focused almost exclusively through the drug container. Instead, a relatively large volume of the electrical field is bypassing the drug container, and large tolerances of distances of the electrodes to the drug container are permitted. Surprisingly, the measurement of impedance via the applied electrical field in the present invention is precise and repeatable enough to measure the liquid volume down to 1 µl, preferably to 0.1 µl precision. In a typical insulin pen at a concentration of 0.1 U/µl, this translates to a precision of 0.1 to 0.01 U (with U being the international unit for the amount of a substance, as known to a person skilled in the art).

As described above, the inventive device is a (separate) device for attachment to a portable liquid injection device, in particular for attachment to a so-called insulin pen. As a consequence, the inventive device can be e.g. in the form of a sleeve which is attached to the injection device for enclosing the drug reservoir of the injection device completely. With these embodiments, the sleeve has at least two flat conductive electrodes enabling an electrical field to be applied across the drug reservoir. With these embodiments, the sleeve can be pushed onto the insulin pen and positioned on the part of the pen which holds the drug reservoir, e.g. for insulin.

In preferred embodiments of the present invention, the inventive device is in the form of a cap, in particular in the form of a cap of an insulin pen. The term "cap" means any (separate) component to be attached to an injection device, preferably an insulin pen, which covers (and normally protects) another critical component or part of the injection device, e.g. the needle for injecting the corresponding substance. With an insulin pen, a cap normally covers the needle as well as at least a part of the drug reservoir of the pen. This aspect of the invention will be explained in more detail later.

According to further preferred embodiments of the invention, the inventive device is replaceable. This means that the device can reversibly be attached to the injection device, i.e. the device can be removed from the injection device and attached to the injection device again and again, if necessary.

Further, it is preferred that the inventive device has an outer electrical shield located on the far side of the device with respect to the (stimulating) electrodes. Such shield acts as a Faraday cage shielding the electrodes from external interference and avoiding any impedance changes caused by factors located outside of the device.

Further, the inventive device comprises an electric circuitry to which inter alia the (stimulating) electrodes are connected. The inventive device, in particular the electric circuitry, comprises at least one battery (non-rechargeable or rechargeable). Also other power sources are possible according to the present invention.

In further preferred embodiments of the present invention, at least one additional guard electrode is provided to the inventive device. Such guard electrodes preferably are connected to a separate electric feeding circuitry and are held at a potential equal to the stimulating electrodes. Such guard electrodes focus the electrical field between the impedance electrodes to force it through the drug reservoir.

Said guard electrodes are being kept at the same electrical potential as the stimulating electrodes mentioned before, but normally using a separate electrical source circuitry. With this arrangement of additional guard electrodes it is possible to focus the electrical field into the desired volume of a drug reservoir. In this context, it is preferred that (also) the guard electrodes are provided in pairs as already explained above relating to the (stimulating) electrodes. All these aspects of the present invention will be discussed in more detail later.

Further, according to the invention, an impedance measurement circuitry can be provided to the inventive device. With this circuitry, the impedance measurement is performed, preferably using a sine or rectangular AC stimulation at a frequency of 5 to 50 kHz and a peak to peak voltage of 0.2 to 30 V (Volt).

The impedance measurement is preferably performing a lock-in measurement in order to measure a signal exclusively at the desired frequency and phase.

The impedance measurement circuitry includes preferably a capacity compensation circuitry for driving the stray capacitances thus minimizing the alternating current in the measurement circuitry caused by stray capacitances and increasing the signal to noise ratio.

Further, the inventive device preferably comprises a flexible printed circuit board (PCB). Such PCB can be easily integrated into the inventive device as a substrate for all necessary equipment, e.g. not only including all circuitry, but also the electrodes on such PCB.

As a consequence, it is preferred that said flexible PCB is adapted to a sleeve-like or a cap-like component, wherein preferably said flexible PCB is molded or mounted into said sleeve-like or cap-like component.

In addition, according to the present invention, it is preferred that the device comprises at least one display.

In further preferred embodiments of the invention, the inventive device is designed to substitute at least one existing cap of an existing insulin pen. This means that the inventive device, on the one hand, includes all equipment, including the electrodes, necessary according to the present invention, but, on the other hand, corresponds in all other design elements to the existing cap of the existing insulin pen. In other words: The present invention refers to a facultative add on to existing insulin pens. The inventive device can be produced to fit any insulin pen on the market. It allows the user to handle the pen as before, without interference or changed user procedure. In particular, the approved liquid injection device is not altered, the dosage mechanism and its display are not interfered with, and the handling/usage procedure remains unchanged.

As described above, it is the main aspect of the present invention to determine the filling state of the drug reservoir of the injection device. However, the impedance changes detected with the inventive device cannot be used only for determining the filling state of the drug reservoir. Those changes which can be detected according to at least one algorithm in an electronic data processor, can be also used to detect at least one of the following conditions or activities which are typical in the use or handling of an insulin pen, namely:

injection (corresponding to a change in the filling state of the drug reservoir), removal of the inventive device from the liquid injection device, in particular of the cap, (decapping), attachment of the inventive device to the liquid injection device, in particular of the cap (recapping), check for remaining (liquid) drug in the inventive device, in particular the cap (e.g. check for contamination), check for a so-called air shot (priming of the injection device/its needle), detection of a decrease in the drug (solution) volume typical for an injection and/or air shot, detection of an increase in the drug (solution) volume typical for a re-filling procedure and/or for insertion of a new injection device, in particular pen, into the inventive device, in particular the cap, detection of temporary changes in impedance typical for external manipulations, e.g. detection of human tissue in the proximity of the inventive device, detection of changes in impedance correlated to temperature changes.

Further, the inventive device can include at least one of the following features, namely:

a power on-mechanism activating only upon opening a package enclosing the inventive device, a so-called reed contact, push buttons to scroll through at least one data base on a corresponding display, at least one memory unit, at least one timer unit, at least one temperature compensation unit, at least one USB (Universal Serial Bus) or any other wired communication unit to transfer data to an external computer or mobile calculator, at least one wireless communication unit to transfer data to an external computer or mobile calculator, e.g. blue-tooth.

In other preferred embodiments of the present invention, the inventive device is composed of at least two parts connecting together to form the device, in particular the cap. In this context, it is preferred that the inventive device includes two parts.

Preferably at least one cavity is formed between the parts for holding other components of the device, e.g. for holding a battery, a display or other units like a timer unit.

The inventive device is preferably made of a plastic material, in particular of a plastic material formed by injection molding.

Further, it is preferred that the inventive device includes means for fixing, especially for reversibly fixing the device to another item and, therefore, holding the device, in particular the device attached to the injection device on that other item. Preferably, such means are in the form of a pocket clip.

As already described, the inventive device can include a cavity being a compartment for a battery or another power source. Preferably, such compartment has a cover holding the battery or other power source in place.

As already mentioned, the inventive device can comprise at least one display. Preferably, such display is a liquid crystal display (LCD), in particular a four-digit digital LCD.

Finally, the invention includes a portable liquid injection device, in particular an insulin pen, which comprises the inventive device as described above, wherein preferably said inventive device is attached to the injection device, in particular to the insulin pen.

The inventive device in its various embodiments brings a number of benefits to the users of portable liquid injection devices, in particular insulin pens.

As already explained, a typical example for a patient dosage pattern is as follows:

In the morning the patient injects a dose of long-lasting insulin with his/her first pen. During the day he/she further injects multiple doses of rapid acting insulin before each meal. Timing and doses are typically similar from day to day for the same patient. Deviation from this pattern would be dangerous. The wrong pen could be used, or the wrong dose injected, or the injection either forgotten or doubled. In all those cases of error the inventive device having up-to date data e.g. relating to the filling level of the drug reservoir and ideally having learned the typical daily dose pattern can recognize a deviation and warn the patient. The patient can then contact his doctor for advice, or administer glucose or insulin for correcting the error, thus avoiding a hypoglycemic shock or dangerous hyperglycaemic states. In this case of two different pens with e.g. a long-lasting and a rapid-acting insulin two inventive devices will be used, one on each pen respectively. The two devices can communicate wirelessly in order to receive and survey complete dosage information including dosage information from the other pen. One device could be a master with additional features like displays etc. while the other devices could be variants as a slave device.

In another embodiment the devices can communicate with a third device e.g. a smartphone or a blood glucose meter and the dosage pattern logic including alarm functions can then be also implemented in a third device.

In other preferred embodiments, the inventive device comprises intelligent features, i.e. the device contains a microprocessor and an algorithm that can recognize and automatically learn the typical pattern of time and dosage for a given patient. Alternatively a typical pattern can be programmed into the device as well as alarm thresholds, e.g. by wireless data communication. In addition, the airshot pattern used by this patient (squirting a small amount of insulin into the air before injection to prime and test the hypodermic needle) will be programmable. The device will contain a microprocessor running algorithms that analyze the dosage and time and warn the patient when deviating from his typical dosage pattern using an alarm feature. The device comprises means for acoustical, optical or vibrational warnings and alarms.

As mentioned, frequently a patient uses two or more different injection pens containing at least a long-lasting (pen A) and a rapid acting insulin (pen B) respectively. The inventive device then may comprise means featuring a key lock mechanism. A matching device will remain on the pens and allow only the fitting of cap A to pen A and cap B to pen B, excluding confounding the two pens with different types of insulin. The aforementioned key lock mechanism could comprise a plastic ring or sleeve that remains permanently on the pen and contains geometric features that ensures fitting the correct cap to its respective pen only.

Thus, multiple different devices could be used on different pens with different types of insulin. Wireless communication between these devices can ensure that the right pen is used at the correct time and dose and deviations from the correct dosage and time pattern will trigger alarm.

Further, a biometric identification of the patient can be provided by e.g. a fingerprint sensor on the cap or an additional device to exclude confounding or tampering with data belonging to patient.

Further advantages and features of the invention will become clear from the following description of the drawings in conjunction with the dependent claims. The individual features can be realized either singly or separately in combination in one embodiment of the invention. The drawings merely serve for illustration and better understanding of the invention and are not to be understood as in any way limiting the invention.

Figure 2:
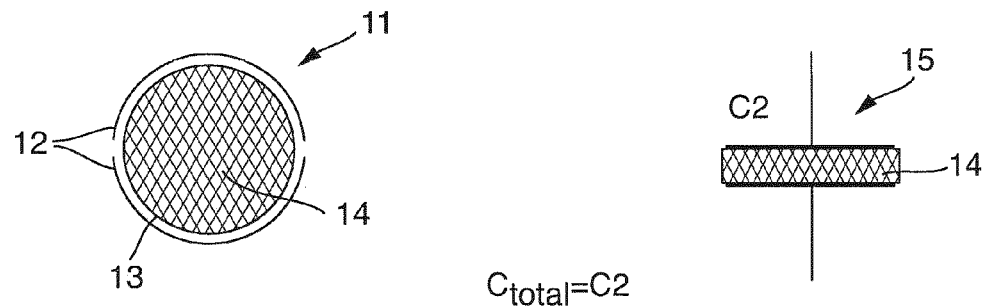
Figure 3:
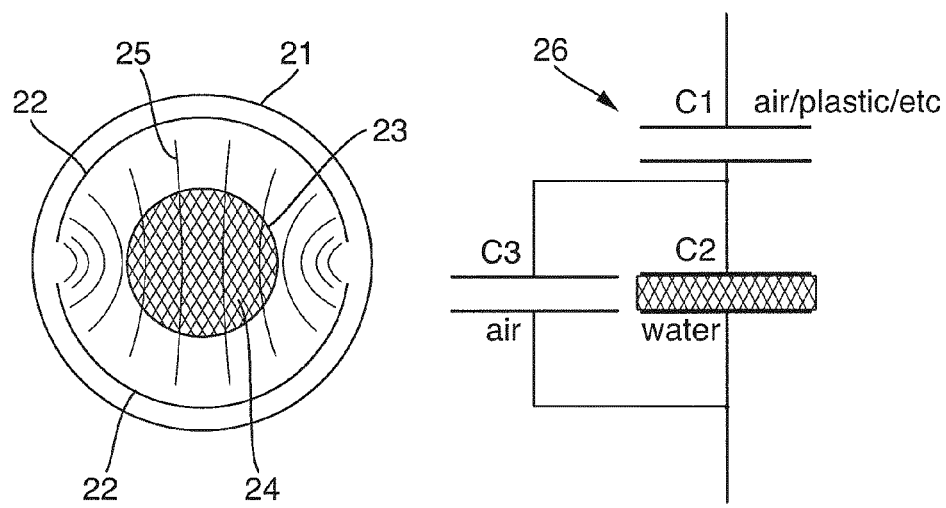
Figure 4:
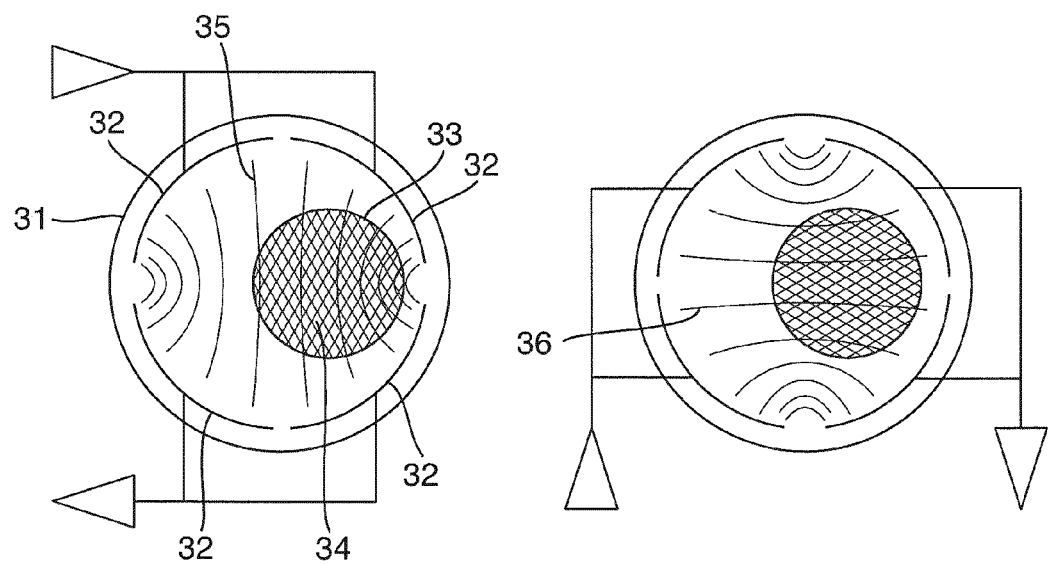
Figure 5:
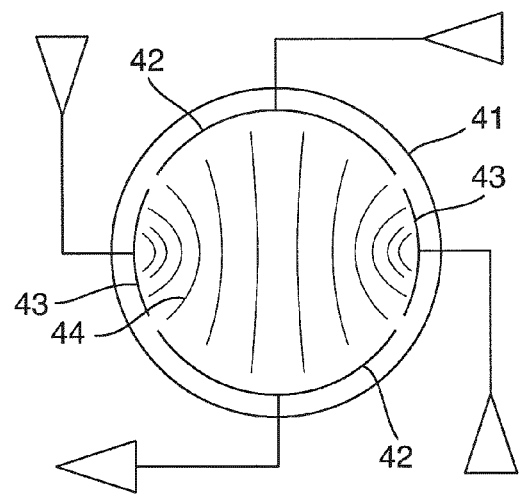
Figure 6:
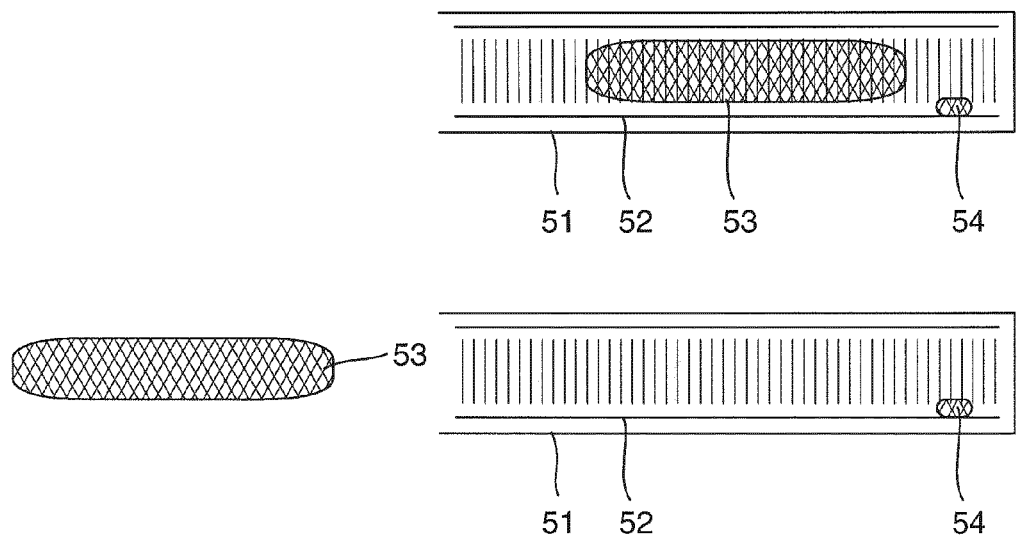
Figure 7:
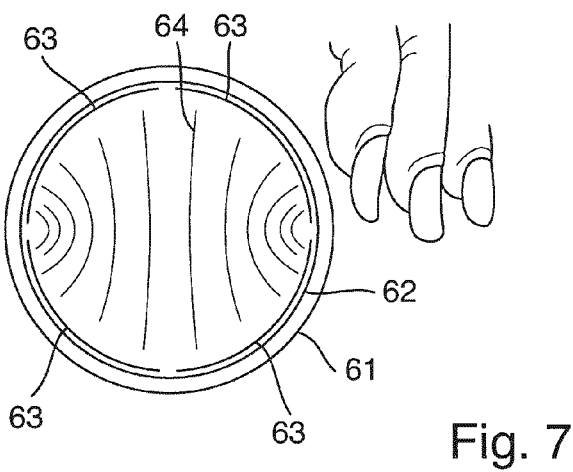
Figure 8:
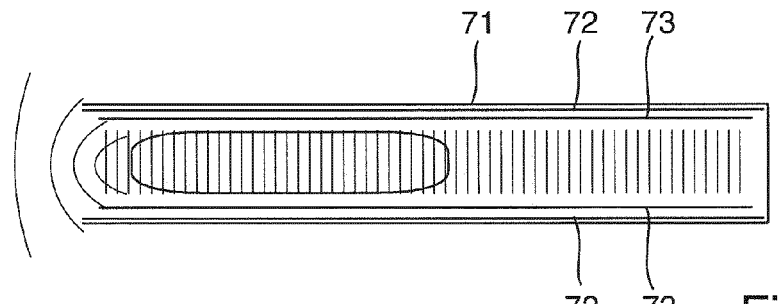
Figure 9:
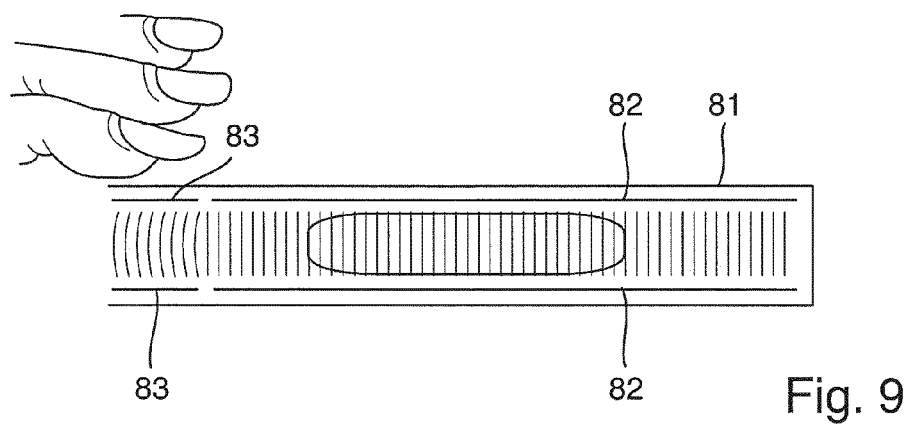
Figure 10:
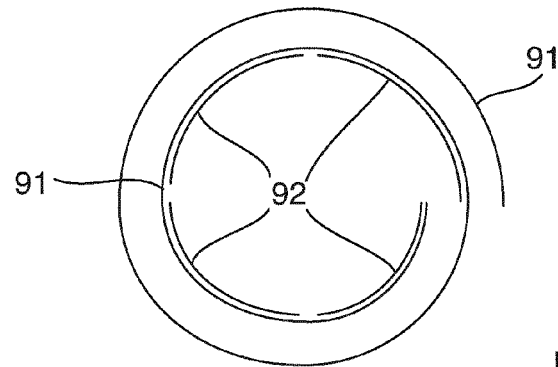
Figure 11:
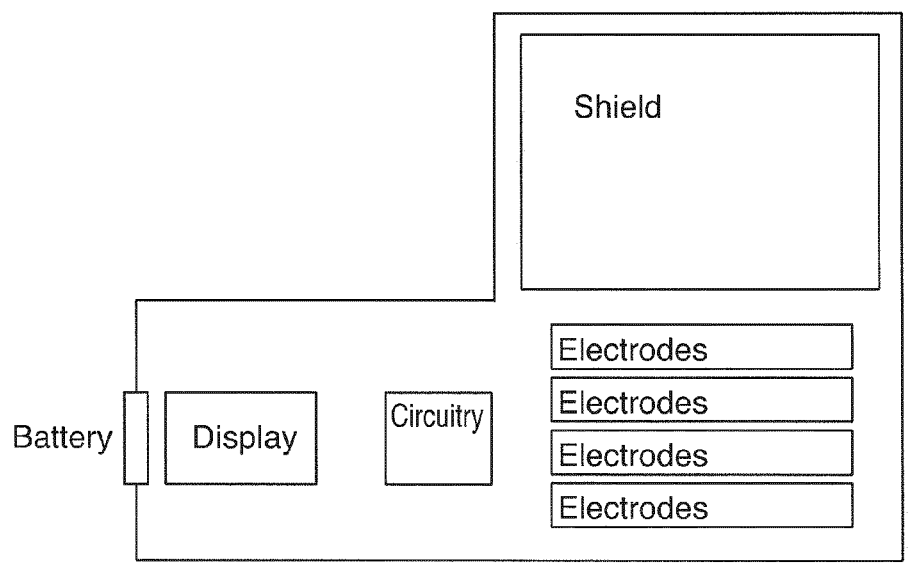
Figure 12:
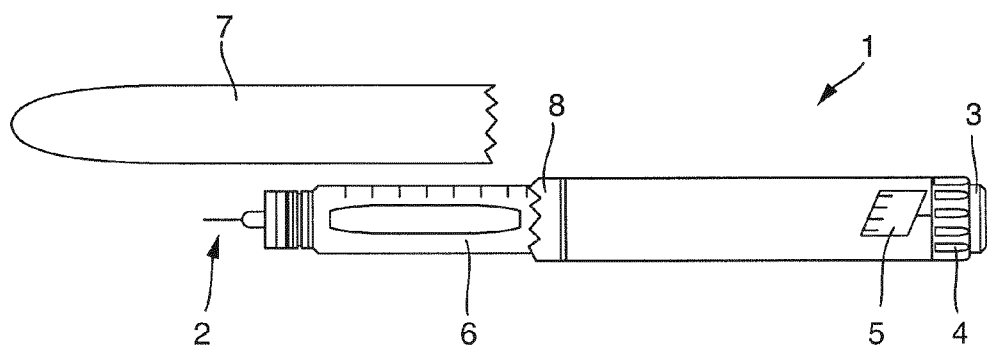

The figures schematically show:

FIG. 1 an insulin pen and its cap according to the state of the art,

FIG. 2 the drug reservoir of a portable liquid injection device with electrodes integrated into the surface of the drug reservoir, and its illustration as a capacitor (both in a sectional view), FIG. 3 an inventive device enclosing the drug reservoir of an insulin pen, and its illustration in a capacitor diagram (both in a sectional view), FIG. 4 another inventive device enclosing the drug reservoir of an insulin pen, wherein two pairs of electrodes are provided (in a sectional view), FIG. 5 another inventive device with additional guard electrodes, FIG. 6 an illustration how the inventive device can be used in a check for contamination, FIG. 7 an illustration how the inventive device can be used for the detection of human tissue in the proximity of the device, FIG. 8 an illustration how the inventive device can be vulnerable to interference from an outside disturbance because of an inhomogeneous or disturbed electrical field on the outside of the inventive device, FIG. 9 an illustration how an inhomogeneous or disturbed electrical field at the inventive device can be avoided and/or compensated via additional guard electrodes, FIG. 10 another inventive device wherein a flexible PCB is used (in a sectional view), FIG. 11 main components of the inventive device located on a flexible PCB according to the invention, and FIG. 12 an insulin pen and its cap with a key-lock mechanism which can be implemented with an inventive device.

In FIG. 1, a typical insulin pen 1 according to the state of the art is shown. As mentioned earlier, an insulin pen is used to inject insulin for the treatment of diabetes. As is well-known, insulin is a hormone produced by the pancreas. It is important for regulating carbohydrate and fat metabolism in the body.

Insulin pen 1 according to FIG. 1 has a needle 2 at its one end and a button 3 for actuating the injection at the other end. Further, in FIG. 1, a dosage knob 4 and a dose window 5 are shown.

Further, insulin pen 1 has a drug reservoir 6 containing the insulin to be injected into the patient. It is the filling level/filling state of this drug reservoir which shall be monitored according to the present invention.

The insulin pen 1 according to FIG. 1 also has a cap 7 which is used according to the prior art to cover the part of the pen comprising the needle and the drug reservoir.

FIG. 2 shows an embodiment of a liquid injection device 11 (e.g. an insulin pen) in which two electrodes 12 are closely arranged to or integrated into a drug reservoir 13 which is at least partly filled with a drug 14 in liquid form.

As discussed earlier, the two electrodes 12 form a capacitor 15 with the drug solution 14 being the bulk of the dielectric material in this capacitor.

The drawing on the left side of FIG. 2 shows the embodiment of the state of the art injection device (in a sectional view) and the right drawing in FIG. 2 illustrates the corresponding capacitor (also in a sectional view). The capacitance of this capacitor is C2 being the total capacitance according to this embodiment.

In contrast to FIG. 2, FIG. 3 shows an embodiment according to the present invention.

In the drawing on the left side of FIG. 3, a cap 21 for an insulin pen is shown in a sectional view. This cap 21 has two flat conductive electrodes 22 enclosing the drug reservoir 23 of the insulin pen. Preferably the electrodes are in the shape of a cylindrical surface segment. The drug reservoir 23 is at least partly filled with insulin 24 (in an aqueous solution).

As it can be seen from FIG. 3, the two electrodes 22 are elongated electrodes which are provided to be parallel to the longitudinal axis of the insulin pen. The two electrodes 22 enclose the drug reservoir 23 and they are enabling an electrical field to be applied across the drug reservoir 23 of the insulin pen.

It is clear from the left drawing of FIG. 3 that in contrast to the embodiment of FIG. 2 (left drawing) the two electrodes 22 are distant from the drug reservoir 23. Nevertheless, it is possible to measure the differences in capacitance resulting from a change in the filling level of drug 24 in drug reservoir 23.

Further, in the left drawing of FIG. 3, the field lines 25 and their pattern is schematically shown in this drawing.

In the drawing on the right side of FIG. 3, the capacitors contributing to the total capacitance of the embodiment according to FIG. 3 (diagram 26) are shown. The illustration on the right side of FIG. 3 corresponds to the sectional view of the embodiment on the left side of FIG. 3.

The equation for the total capacitance ($C_{total}$) depending from the contributing capacitors is also reproduced in FIG. 3. Referring to the disclosure of FIG. 3, it has to be mentioned that normally the total capacitance to be measured is quite small, i.e. it is in the sub-picoFarad to sub-femtoFarad range. Further, the signal to noise ratio is quite small, when capacitance C2 changes, i.e. such changes are in the femtoFarad range.

FIG. 4 shows another embodiment according to the present invention. This embodiment is a preferred solution for the problem that rotational and lateral tolerances normally have to be considered when electrodes are placed quite far away from the drug reservoir, e.g. are placed in the cap of an insulin pen, and stray capacitances are large and variable.

Therefore, according to the embodiment of FIG. 4, a cap 31 for an insulin pen has four conductive electrodes 32 enclosing drug reservoir 33 which is at least partly filled with insulin 34 in liquid form.

The disposition of the four electrodes 32 can also be alternatively described as a disposition of two pairs of two electrodes enclosing the drug reservoir of the corresponding insulin pen.

An important advantage of the embodiment according to FIG. 4 is that electrodes 32 can be combined (switched) to apply an electrical field at different rotational angles. The corresponding measurement values (readings) at these different angles can be mathematically combined, preferably averaged. As a result, rotational and lateral tolerances, together with an inhomogeneous field resulting in variations of capacitance at a constant filling level of the insulin container, can be excluded by these measurements and the filling level of the container can be accurately determined instead of those tolerances.

This approach is also shown in FIG. 4. On the left side, the two upper electrodes 32 and the two lower electrodes 32 are electrically combined being connected to a single operational amplifier input or output, respectively, and the corresponding field lines 35 are running in a vertical direction. In the drawing on the right side of FIG. 4, the two electrodes 32 on the left side and the two electrodes 32 on the right side are combined and, therefore, the field lines 36 of the electrical field are running horizontally.

A further embodiment of the present invention is shown in FIG. 5. According to this embodiment, a cap 41 has two conductive electrodes 42 and two (additional) guard electrodes 43. Electrodes 42 on the one hand and guard electrodes 43 on the other hand, both use a separate electrical source circuitry. This fact is graphically illustrated by the operational amplifier symbols in FIG. 5, namely the two operational amplifiers on the top and bottom of FIG. 5 for the two electrodes 42 and the two operational amplifiers on the left and right side of FIG. 5 for the guard electrodes 43.

As it can be seen from the drawing on the left side of FIG. 3, the electrical field is quite inhomogeneous in the gap between the two electrodes 22 on the left side and on the right side. This inhomogeneity can be minimized by the use of the guard electrodes 43 according to FIG. 5. The guard electrodes 43 are introduced into the embodiment with the two conductive electrodes 43 to focus the electrical field into the desired volume enclosing the drug reservoir of the insulin pen (the drug reservoir is not shown in FIG. 5). The guard electrodes 43 are kept at the same electrical potential as the stimulating (conductive) electrodes, however using a separate electrical source circuitry.

The resulting electrical field with minimized inhomogeneity is shown in FIG. 5 via the field lines 44.

FIG. 6 illustrates the situation when incidentally a drop of liquid is placed outside the drug reservoir, e.g. in the cap. Such drop can be a drop of the drug which is now outside the drug reservoir or a drop from another liquid, e.g. water.

The present invention can solve this problem by a differential measurement which is made with the inventive cap attached to the insulin pen and with the inventive cap separately.

In this context, the upper drawing shows the situation in which the cap 51 with its electrodes 52 is attached to the insulin pen. In this case, cap 51 encloses drug 53 in the drug reservoir completely. However, cap 51 also encloses the (additional) drop 54.

In this arrangement, a first measurement by applying an electrical field is made.

Afterwards, an additional measurement on the cap is made separately, i.e. after the cap 51 has been detached from the insulin pen. As a consequence, only the additional drop 54 contributes to this measurement. Drug 53 in the drug reservoir does not contribute to this second measurement. This situation is shown in the drawing at the bottom of FIG. 6.

By comparing the two measurements, e.g. by "subtracting" the contribution of the drop from the first measurement, the real filling level in the drug reservoir of the insulin pen can be determined.

FIG. 7 shows a solution for the problem that there is a disturbing influence on the electrical field from outside the electrode array. This influence can also result from an (outside) liquid or e.g. from human tissue like a finger.

To solve this problem an additional shield 62 can be provided outside the electrodes 63 in an inventive cap 61. As a consequence, the electrical field represented by the field lines 64 in FIG. 7 will not be affected by the influence from outside.

FIG. 8 illustrates the solution of the problem that the electrical field provided by the conductive electrodes in a cap for an insulin pen can be inhomogeneous or disturbed at the open end of said cap. This problem can be solved according to the embodiment of FIG. 8 in that a shield 72 is placed into cap 71 between the inner surface of the cap 71 and the electrodes 73 in the cap. Shield 72 can be a separate device provided in the cap 71 or e.g. can also be a coating on the inner surface of cap 71.

According to the embodiment of FIG. 8, there is a longitudinal overlap of the shield 72 over the electrodes 73 in the cap 71. This fact is shown on the left side of FIG. 8.

Further, according to FIG. 8, there is also an overlap of the electrodes 73 over the longitudinal extension of the reservoir which is also shown on the left side of FIG. 8.

In other words: According to the embodiment of FIG. 8, the shield 72 provided in the cap is "longer" than the electrodes 73 provided in the cap 71, and the electrodes 73 are "longer" than the extension of the drug reservoir into the direction of the open end of cap 71. By these measures (separately or in combination), the inhomogeneities of the electrical field at the open end of cap 71 (left side in the drawing of FIG. 8) and/or their influences on the capacitive determination of the filling status of the drug container can be minimized.

Another measure for solving the problem of field inhomogeneity or field disturbance at the open end of an inventive cap is shown in FIG. 9. Here, as an example, a human finger is located in a field inhomogeneity that could affect the measured impedance between electrodes 82 (see FIG. 8).

As a solution, FIG. 9 shows an embodiment in which cap 81 (having an additional shield or not) comprises not only (stimulating) electrodes 82, but also guard electrodes 83. These guard electrodes 83 focus the electrical field between the electrodes 82 at the open end of cap 81 (left side in the drawing of FIG. 9). Guard electrodes 83 ensure that the whole volume of the drug reservoir is enclosed by an electrical field and that this field is not straying out of the cap at its open end (left side in FIG. 9). As already explained, guard electrodes 83 are fed with the same voltage as the respective (stimulating) electrodes 82, but from a separate circuitry. As a consequence, the resulting electrical field for measurement between electrodes 82 is focused into the volume necessary for such measurement.

Still a further embodiment of the invention is illustrated in FIG. 10. Here, a flexible printed circuit board (PCB) 91 is shown. This flexible PCB 91 is wound-up to a cylindrical shape. Such a shape is perfectly designed to fit to a sleeve-like or a cap-like component or to the inner form of such a component, respectively. Preferably, a structure like the flexible PCB 91 can be moulded or mounted into such a component.

On one surface of the flexible PCB 91 electrodes 92 are provided. In another embodiment, they can also be provided on both surfaces or intermediate layers of the flexible PCB. In this context, four electrodes are shown on such a surface of flexible PCB 91. Electrodes 92 can be (stimulating) electrodes or guard electrodes as already explained earlier. If flexible PCB 91 is adapted to or molded/mounted into a cap-like component, electrodes 92 form an array of electrodes which can enclose the drug reservoir of on insulin pen.

As also mentioned earlier, further components of at least one electrical circuitry can be provided on flexible PCB 91.

Further, FIG. 11 discloses a summarizing overview of a preferred embodiment of the present invention schematically. The corresponding components (preferably provided on a flexible PCB) necessarily include electrodes, in the case of the embodiment of FIG. 11 four electrodes. Further, at least one electrical circuitry is necessary for providing electrical energy to the electrodes and for measuring at least the total capacitance. If appropriate, a further circuitry is provided for additional guard electrodes.

Further, the components can include an (outer) electrical shield, and in case at least one display.

Further, at least one power source, in particular a battery or an accumulator, is provided.

Finally, in FIG. 12 an insulin pen and its cap is shown in which a key-lock mechanism as already described above is implemented. Such a key-lock mechanism comprises two parts which match with each other or fit together like a key and its lock so that e.g. confounding two pens with different types of insulin is excluded. Such a key-lock mechanism can be implemented with all embodiments of the already described inventive device.

For the sake of simplicity the insulin pen and its cap have the same reference numbers as the insulin pen and its cap according to FIG. 1. As a consequence, FIG. 12 shows an insulin pen 1 and its cap 7, wherein insulin pen 1 has a needle 2 at its one end and a button 3 for actuating the injection at the other end. Further, in FIG. 12 a dosage knob 4 and a dose window 5 are shown. The drug reservoir of insulin pen 1 is shown with reference number 6.

According to FIG. 12 cap 7 has a characteristic form at its open end at the right side. This characteristic form 7 matches with the characteristic form of a ring or sleeve 8 which is permanently located on insulin pen 1. Only if the characteristic form of the open end of cap 7 fits into the corresponding characteristic form of sleeve 8 on cap 1, it is possible to attach cap 7 according to FIG. 12 on insulin pen 1 according to FIG. 12. If there is no fit or match, the user of the insulin cap will realize that he or she obviously uses the wrong cap for the corresponding insulin pen.

The invention claimed is:

1. A device in a form of a removable cap for attachment to a portable liquid injection device and configured to enclose at least a section of the portable liquid injection device having a drug reservoir and to be removed when an injection is performed, comprising:
    at least two conductive electrodes enabling an electrical field to be applied across an entire volume of the drug reservoir of the portable liquid injection device, wherein the at least two conductive electrodes have a height or thickness lower than any dimension other than the height and the thickness, wherein the at least two conductive electrodes including at least two pairs of conductive electrodes, along a circumference of the device, for forming a capacitor, with a total number being at least 2·n electrodes with n≥2,
    wherein the electrode pairs are disposed on an inner circumferential surface of the removable cap, and are geometrically arranged at angular offsets; and
    at least three conductive electrodes configured to be separately switched to apply electrical field across the drug reservoir in multiple rotational directions perpendicular to the longitudinal axis of an injection device.

2. The device according to claim 1, wherein the at least two conductive electrodes are elongated electrodes, wherein a longest dimension of the electrodes is provided to be parallel with an axis of the portable liquid injection device.

3. The device according to claim 1 wherein the device has an outer electrical shield.

4. The device according to claim 1, comprising an electric circuitry, to which inter alia the at least two conductive electrodes are connected.

5. The device according to claim 1, comprising at least one power source.

6. The device according to claim 1, comprising at least one additional guard electrode connected to a separate electric circuitry.

7. The device according to claim 1 comprising an impedance measurement circuitry.

8. The device according to claim 1, comprising a flexible printed circuit board (PCB).

9. The device according to claim 8, wherein the flexible PCB is adapted to a sleeve-like or a cap-like component, wherein the flexible PCB is molded or mounted into the sleeve-like or cap-like component.

10. The device of claim 8, wherein the flexible PCB is in a cylindrical shape.

11. The device according to claim 1, comprising at least one display.

12. The device according to claim 1, wherein the device is designed to substitute at least one existing cap of an existing insulin pen.

13. A portable liquid injection device, comprising a device according to claim 1, wherein said device of claim 1 is attached to the portable liquid injection device.

14. The portable liquid injection device of claim 13, wherein the portable liquid injection device is an insulin pen.

15. The device of claim 1, wherein the portable liquid injection device is an insulin pen, and the device is a cap of the insulin pen.

16. The device of claim 1, wherein the at least two conductive electrodes are in a cylindrical shape.

17. The device of claim 1, wherein n is between 2 and 10.

18. The device of claim 1, wherein the at least three electrodes are configured to be separately switched so as to rotate the electrical field across the drug reservoir, and provide compensation for rotational, axial and lateral tolerance and/or asymmetry of the injection device inside the removable cap.

19. The device of claim 1, wherein the at least three electrodes are configured to apply alternating current (AC) variable fields across the drug reservoir.

* * * * *